(12) United States Patent
Marchetti et al.

(10) Patent No.: US 10,357,033 B2
(45) Date of Patent: Jul. 23, 2019

(54) MAT STRUCTURE WITH INSECTICIDE

(71) Applicant: The Schawbel Corporation, Bedford, MA (US)

(72) Inventors: Fabio Marchetti, Trento (IT); Cedric Morhain, Barcelona (ES)

(73) Assignee: Thermacell Repellents, Inc., Bedford, MA (US)

( * ) Notice: Subject to any disclaimer, the term of this patent is extended or adjusted under 35 U.S.C. 154(b) by 423 days.

(21) Appl. No.: 14/601,400

(22) Filed: Jan. 21, 2015

(65) Prior Publication Data

US 2015/0201613 A1    Jul. 23, 2015

Related U.S. Application Data

(60) Provisional application No. 61/929,612, filed on Jan. 21, 2014.

(51) Int. Cl.
*A01N 25/34*    (2006.01)
*A01M 1/20*    (2006.01)

(52) U.S. Cl.
CPC .......... *A01N 25/34* (2013.01); *A01M 1/2061* (2013.01)

(58) Field of Classification Search
CPC .............................. A01N 24/34; A01M 1/2061
See application file for complete search history.

(56) References Cited

U.S. PATENT DOCUMENTS

| 5,700,430 | A | 12/1997 | Bonnema et al. | |
|---|---|---|---|---|
| 6,663,838 | B1 * | 12/2003 | Soller | A01M 1/2088 422/120 |
| 2004/0151747 | A1 * | 8/2004 | Davis | A01M 1/2077 424/405 |
| 2005/0005504 | A1 * | 1/2005 | Munagavalasa | A01N 25/18 43/129 |

\* cited by examiner

*Primary Examiner* — Rachael E Bredefeld
(74) *Attorney, Agent, or Firm* — Levisohn Berger LLP

(57) ABSTRACT

A long life mat impregnated with insect repellant is provided which has greater concentration that prior art mats in the area above a heated sole plate in prior art volatilizable insecticide repellant devices.

5 Claims, 2 Drawing Sheets

US 10,357,033 B2

MAT STRUCTURE WITH INSECTICIDE

RELATED APPLICATIONS

This invention claims priority of provisional patent application Ser. No. 61/929,612, filed Jan. 21, 2014, which is incorporated herein.

BACKGROUND AND SUMMARY OF THE INVENTION

This invention relates to an improvement in a mat which holds a volatile substance to be dispersed to repel insects when the mat sits on top of a heated plate and emits the volatile substance.

This invention relates to an appliance for dispensing a volatile substance as shown and described in U.S. Pat. No. 5,700,430, the contents of which are incorporated herein.

The appliance described in the '430 patent includes a sole plate 32 having a mat sitting on heated surface 33, with the heated surface 33 causing a volatile substance in the mat being dispersed through the heating of the mat.

This invention relates to enhancing the mat structure by creating and developing a new mat structure which will extend mat life at least two or three times current mat life.

The new long life mat (hereinafter LLM) is almost twice as long as the standard mat currently available. In particular, the long life mat is approximately nine centimeters long while the current four hour mat is five centimeters long.

In the new structure, the LLM extends beyond the plate 32 by approximately two centimeters on each side, and it may drape on the side of the appliance.

DETAILED DESCRIPTION OF THE PREFERRED EMBODIMENT

Figure 1:
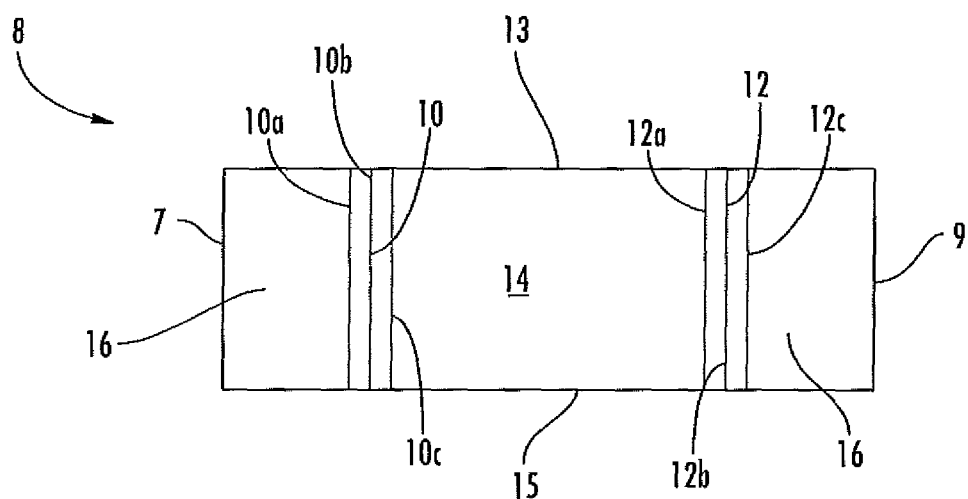
FIG. 1 illustrates a top view of the new mat.
Figure 2:
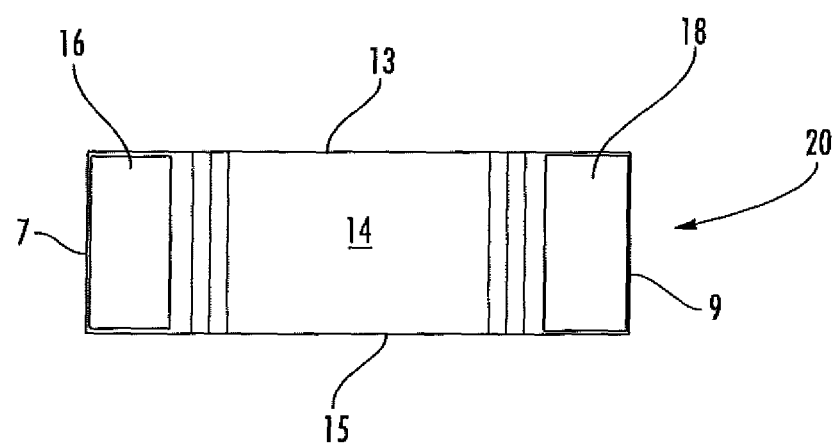
FIG. 2 shows a top view with a plastic layer thereon.

Referring to FIG. 1, the new mat 8 is approximately nine centimeters from outer edges 7 and 9.

There are vertical transverse boundaries 10 and 12 that span the mat from top edge 13 to bottom edge 15. Such boundaries, illustratively, are approximately five centimeters apart creating a central area 14 while the distance from boundaries 10 and 12 to outer edges 7 and 9 respectively, is approximately two centimeters each.

Boundaries 10 and 12 are integrally formed as barriers with the mat 8 by a plurality of parallel boundary structures 10a, 10b, 10c and 12a, 12b and 12c shown in FIG. 1 spanning from top edge 13 to bottom edge 15. These boundaries impede the volatile substance impregnated on the mat between boundaries 10 and 12 from migrating outwardly beyond the boundaries. Capillary transmission is impeded by boundaries 10 and 12.

The mat 8 itself may be fibrillar substrate, for example, made of cellulous although any porous material which can hold a volatile substance such as a substrate made of fibers of synthetic polymers, open cell foam or other materials could be used. The boundaries 10 and 12 may be formed of the same cellulous material as the mat, except the boundaries will be highly compressed, forming for example, three parallel raised protrusions which impede the flow of insecticide from central area 14.

The central area 14 of the mat is of the same five cm width currently available for prior art sole plates which have a heated surface (elements 32 and 33 of the '430 patent).

By increasing the length of the mat from five to nine centimeters, the amount of volatile substance in mat 8, especially in central area 14 can also be increased, and by compressing and maintaining it within region 14 of FIG. 1. The concentration of volatile substance is greater while the boundaries 10 and 12 impede migration of the volatile substance outside the boundaries 10 and 12.

Areas 16 and 18 outside the boundaries ensure safe manual handling of the mat since substantially no insecticide is located in areas 16 or 18 and the mat can safely be lifted or manually handled.

Figure 3:
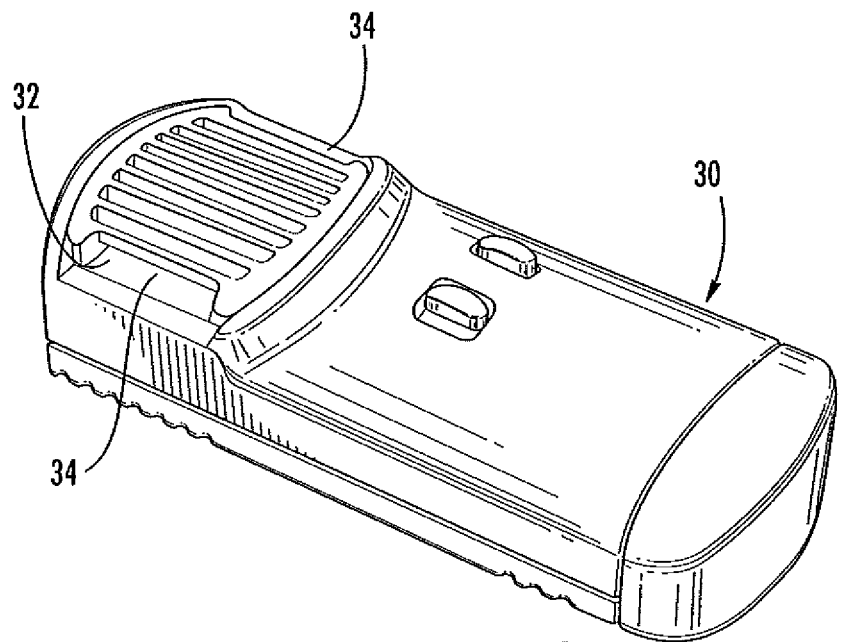
FIG. 3 is a perspective view of the insecticide dispensing device of the prior art.

Further, a plastic layer 20, shown in FIG. 3, may be added both on top and bottom of the lateral areas 16 and 18 which helps avoid manual touching insecticide area 14 of the mat.

With the long life mat being nine centimeters long, and the mat being used with conventional prior art devices, especially heated sole plates, there will be approximately a two centimeter overhang 16 and 18 on each side of the mat 8. Since the overhanging parts are not heated, concentration of the active ingredient within the central area 14 provides overall greater concentration of the volatile substance in that area and extends the life of the mat at least two fold over current mats.

If the mat is stiff, the side areas 16 and 18 will stick out, but one could provide a natural bend area permitting the sides 16 and 18 to drape on the sides of the appliance 30.

A mat is an inert material, and the active ingredient impregnates the mat. The ratio of active to inert ingredient is increased by providing a longer mat yet restricting the active ingredient to the smaller area 14, thus providing greater concentration of the active substance.

The present invention takes advantage of the widespread use of prior art devices already in the market having a sole plate of approximately five centimeters in width. By providing the improved LLM, the LLM may be used with standard preexisting appliances which will enable the new LLM to be slid onto the sole plate 32 through slot 34 with the overhanging two centimeters in regions 16 and 18 either draping on the sides of the device or extending therefrom.

Figure 4:
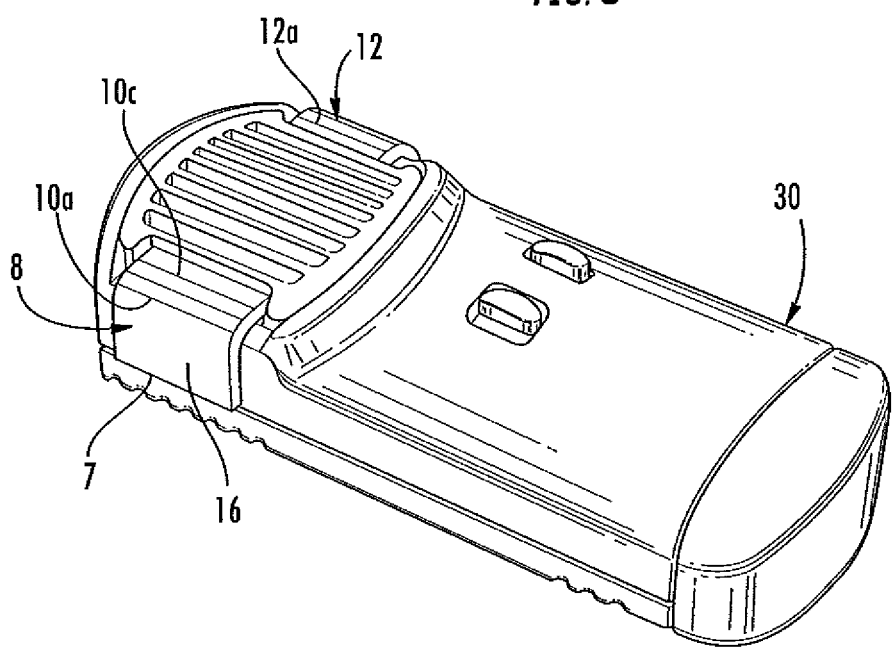
FIG. 4 is a view similar to FIG. 3 with the mat of this invention in place.

FIGS. 3 and 4 are perspective views of the prior art insect repellent appliance which is the subject of U.S. Pat. No. 5,700,430, the contents of which are incorporated herein. The device 30 has a sole plate 32 under the grill as shown and has side slots 34. The side slots allow the mat 8 of this invention to slide through under the grill through slots 34 with an overhang of segments 16 on the left side as shown and 18 (on the other side of the grill which is not seen). Boundaries 10 and 12 are located between areas 16 and 18 and the heated sole plate 32, and finger handling sections 16 and 18 are then utilized to slide the mat through the slot 34 around allowing for the overhangs as described above. Segments 16 and 18 may be stiff enough to extend straight out beyond the sides of the appliance 30 to provide easily accessible manual handles to manipulate the mat.

It should be understood that the preferred embodiment was described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly legally and equitably entitled.

The invention claimed is:

1. An insecticide dispensing apparatus having a heated sole plate and a mat impregnated with insecticide to be dispensed when said mat sits flat on and is heated by said heated sole plate, said sole plate having a width, said mat having a rectangular shape and being made of a porous cellulose material and comprising:

i.) a central area sized to conform to the width of said sole plate;

ii.) said insecticide being impregnated solely in said central area of the mat;

iii.) two side areas integrally formed with said central area being of the same material as said central area to increase the total length and size of said mat, wherein said side areas are located on both sides of said central area, and the length of each side area comprises about 20% of the length of the entire mat; and iv.) barriers formed on both sides of said central area blocking migration of insecticide in said central area from reaching said side areas, wherein each barrier comprises a boundary structure extending from top to bottom of said mat, and wherein said boundary structure comprises highly compressed cellulose material;

and wherein said mat length is approximately equal to the width of said sole plate plus the width of said barriers plus the length of said side areas.

2. The insecticide dispensing apparatus according to claim 1, wherein said central area is approximately five centimeters in length.

3. The insecticide dispensing apparatus according to claim 2, wherein said side areas are equal in length to each other.

4. The insecticide dispensing apparatus according to claim 3, wherein said side areas are each approximately two centimeters in length.

5. The insecticide dispensing apparatus according to claim 1, wherein each of said barriers comprises two adjacent parallel boundary structures extending from top to bottom of said mat.

* * * * *